United States Patent [19]

Dabee et al.

[11] Patent Number: 5,672,770
[45] Date of Patent: Sep. 30, 1997

[54] PROCESS FOR THE PREPARATION OF METHYL 1,1-DICHLOROMETHYL ETHER OR OF ETHYL 1,1-DICHLOROMETHYL ETHER

[75] Inventors: Annick Dabee, Itteville; Patricia Gauthier, Cerny; Jean-Pierre Senet, Buthiers, all of France

[73] Assignee: Societe Nationale des Poudres et Explosifs, Paris Cedex, France

[21] Appl. No.: 545,478

[22] Filed: Oct. 19, 1995

[30] Foreign Application Priority Data

Nov. 4, 1994 [FR] France .................. 94 13210

[51] Int. Cl.$^6$ .................. C07C 43/04; C07C 43/12
[52] U.S. Cl. .................. 568/676
[58] Field of Search .................. 568/676

[56] References Cited

U.S. PATENT DOCUMENTS 5,196,611  3/1993  Henkelmann et al. .................. 568/663

FOREIGN PATENT DOCUMENTS 005647  9/1965  United Kingdom .

OTHER PUBLICATIONS

Journal of Organic Chemistry, vol. 23, No. 5, 22 May 1958 Easton US, pp. 745–746, L.R. Evans et al "Preparation of certain polychloro–dimethyl ethers".

"Organic Syntheses vol. 47" 1967, John Wiley, New York, p. 47—p. 49.

*Primary Examiner*—Marianne M. Cintins
*Assistant Examiner*—Dwayne C. Jones
*Attorney, Agent, or Firm*—Bucknam and Archer

[57] ABSTRACT

The invention relates to a process for the preparation of methyl 1,1-dichloromethyl ether or of ethyl 1,1-dichloromethyl ether, according to which methyl formate or ethyl formate is reacted with phosgene, diphosgene, triphosgene or oxalyl chloride or one of their mixtures, at a temperature of between 40° C. and 100° C., in the presence of a catalyst chosen from the group consisting of trisubstituted phosphine oxides and sulphides, trisubstituted phosphine dichlorides, formamides, the products of reaction of formamides with chlorinating agents and mixtures thereof. The 1,1-dichloromethyl ethers are obtained in a high purity. They are useful especially for performing the formylation of aromatic compounds.

12 Claims, No Drawings

PROCESS FOR THE PREPARATION OF METHYL 1,1-DICHLOROMETHYL ETHER OR OF ETHYL 1,1-DICHLOROMETHYL ETHER

The invention relates to a new process for the preparation of methyl 1,1-dichloromethyl ether ($CH_3$—O—$CHCl_2$) or of ethyl 1,1-dichloromethyl ether ($C_2H_5$—O—$CHCl_2$).

According to the paper published in J. Org. Chem. 1958, 23, pp. 745–746, it is known to prepare methyl 1,1-dichloromethyl ether by photochemical chlorination of methyl chloromethyl ether.

The reaction scheme is the following:

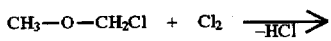

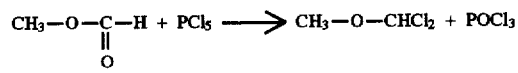

This process exhibits serious disadvantages. The methyl chloromethyl ether employed as starting material is a carcinogenic compound. The reaction yield is very low especially because bis(chloromethyl) ether is also formed. The latter is, moreover, very highly carcinogenic and its presence in a commercial product is prohibited.

The preparation of ethyl 1,1-dichloromethyl ether by this process is still more difficult because of the chlorination which takes place on the ethyl radical and which gives rise to a number of secondary products.

This process is consequently unusable in practice.

Another process has been described in the paper published in Org. Synth. Coll. Vol. V, pp. 365–367 and in the CA abstract No. 55 : 18557f. It consists in performing the chlorination of the formate with phosphorus pentachloride according to the following reaction scheme:

$CH_3$—O—$\underset{\underset{O}{\|}}{C}$—H + $PCl_5$ ⟶ $CH_3$—O—$CHCl_2$ + $POCl_3$ However, this laboratory process is difficult to adapt to an industrial scale. Phosphorus pentachloride is a highly hygroscopic solid which is consequently dangerous to handle. The large quantities of phosphorous effluents which are formed must be treated. 1,1-Dichloromethyl ethers decompose rapidly in the presence of large quantities of $PCl_5$ and/or $POCl_3$, which makes them difficult to isolate from the reaction mixture. In addition, they are obtained in a purity which is not satisfactory because they contain a certain quantity of phosphorus compounds.

There was therefore a need for a process for the preparation of 1,1-dichloromethyl ethers which does not exhibit the disadvantages of the previous processes.

The subject of the invention is a process for the preparation of methyl 1,1-dichloromethyl ether or of ethyl 1,1-dichloromethyl ether, according to which methyl formate or ethyl formate, respectively, is reacted with phosgene, diphosgene, triphosgene or oxalyl chloride, or one of their mixtures, at a temperature of between 40° C. and 100° C., in the presence of a catalyst chosen from the group consisting of:

the trisubstituted phosphine oxides and sulphides of general formula (I)

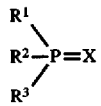

in which X denotes an oxygen or sulphur atom and $R^1$, $R^2$ and $R^3$, which are identical or different, denote a substituted or unsubstituted aromatic radical, the trisubstituted phosphine dichlorides of general formula (II)

in which $R^1$, $R^2$ and $R^3$ have the abovementioned meaning, the formamides of general formula (III)

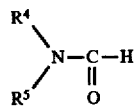

in which each of $R^4$ and $R^5$, which are identical or different, denotes a $C_4$–$C_{10}$ aliphatic radical or a cyclohexyl radical, the products of reaction of the formamides of formula (III) with chlorinating agents, and mixtures thereof.

The reaction scheme is the following:

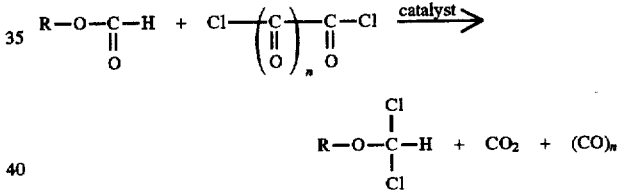

in which R denotes the methyl or ethyl group, n denotes the number 0 or 1,

The process according to the invention permits the industrial preparation, in good yields and a very high purity, of methyl or ethyl 1,1-dichloromethyl ether. The raw materials are cheap. It is easy to use. The treatment of the effluents is simple. The process is consequently economical and the toxic risks are strictly limited to the production unit.

The presence of a catalyst is indispensable for obtaining the 1,1-dichloromethyl ethers. Without the catalyst no reaction is observed in the other conditions of the reaction.

The preferred catalysts of formula (I) are those in which X denotes an oxygen atom.

The substituents of the radicals $R^1$, $R^2$ and $R^3$ are chosen in particular from halogen atoms such as preferably chlorine, bromine or fluorine, $C_1$–$C_4$ alkyl and $C_1$–$C_4$ alkoxy radicals and the nitro group.

The radicals $R^1$, $R^2$ and $R^3$ are preferably identical and preferably denote a substituted or unsubstituted phenyl radical.

Triphenylphosphine oxide, triphenylphosphine sulphide and tri-p-tolylphosphine oxide may be mentioned especially as examples of catalysts of formula (I) which may be employed according to the invention.

The preferred catalyst is triphenylphosphine oxide.

The catalysts of formula (I) or of formula (II) may be bound to a polymer through the intermediacy of one of the radicals $R^1$, $R^2$ and $R^3$. As an example it is possible to mention the polymers which contain a chain sequence:

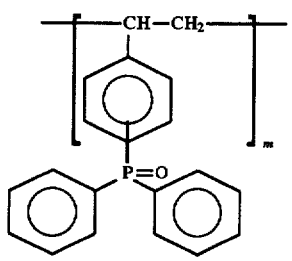

The preferred catalysts of formula (III) are the catalysts in which $R^4$ or $R^5$ denotes a butyl or isobutyl radical or a cyclohexyl radical. Dibutyl- or diisobutyl- formamide and dicyclohexylformamide may be mentioned in particular.

The products of reaction of the formamides of formula (III) with chlorinating agents are obtained in a known manner by reaction of these formamides with chlorinating agents such as, for example, thionyl chloride, oxalyl chloride, phosgene and phosphorus oxychloride. The preferred formamides of formula (III) which are reacted are preferably those in which $R^4$ and $R^5$ denote the radicals mentioned in the paragraph above.

A mixture of a number of the catalysts described above may also be employed.

The catalyst is generally added in a quantity of between 5 and 50% and preferably between 10 and 40 mol % relative to the formate.

The reaction temperature may be between 40° and 100° C. For the preparation of methyl 1,1-dichloromethyl ether it is preferably between 60° C. and 90° C.

The reaction is performed in a liquid mixture. To do this, the operation is carried out at a pressure which is sufficiently high for the formate to be liquid, or an organic solvent is employed which is inert towards the reactants and whose boiling point is sufficiently high to make it possible to obtain the desired temperatures in the reaction mixture.

Chlorobenzene, dichlorobenzenes, trichlorobenzenes and xylenes may be mentioned as suitable solvents. The preferred solvent is o-dichlorobenzene.

The compound which is reacted with the formate is added at least in stoichiometric quantity and preferably in excess in relation to the formate. The preferred reactant is phosgene.

Suitable known devices are employed for making use of the process.

When the reactant is phosgene an appropriate operating method is the following : the solvent, the catalyst and the formate are introduced into the reactor. The reaction mixture is heated to the chosen temperature and gaseous phosgene is then added gradually into the reaction mixture. The reaction is finished after a few hours. The 1,1-dichloromethyl ether is isolated by distillation and is obtained in a very high purity and a good yield.

The applications of the 1,1-dichloromethyl ethers are numerous. One of the most important ones is the formylation of aromatic or heteroaromatic compounds in the presence of a Friedel and Craft catalyst, which makes it possible to obtain the corresponding aldehydes in excellent yields and without interfering by-products.

The examples which follow illustrate the invention without, however, limiting it.

EXAMPLE 1

186 g of o-dichlorobenzene, 22.23 g (0.08 mol) of triphenylphosphine oxide (TPPO) and then 24.37 g (0.41 mol) of methyl formate are introduced at ambient temperature (in the region of 20° C.) into a reactor equipped with stirring and temperature-sensing devices, condensers and feed tubes and the reaction mixture is heated to 68°–70° C. 53.4 g (0.54 mol) of gaseous phosgene are then introduced gradually over 7 hours while the temperature is maintained between 70° and 80° C.

The reaction is followed by gas chromatography (GC) analysis, a standard ($C_8$ alkane) being employed. When the reaction is finished the degree of conversion of methyl formate to methyl 1,1-dichloromethyl ether (MDCME), determined by GC, is 95% and the quantity of unconverted methyl formate, also determined by GC, is 5%.

The MDCME is purified by distillation at reduced pressure. 33.8 g (72% yield) of MDCME which has a purity of 100% (determined by GC analysis) are obtained.

EXAMPLES 2 TO 6

By operating in a manner similar to that of Example 1, tests were performed with various catalysts by varying the proportions of the constituents and the operating conditions. The latter, and the results obtained, are shown in the following table:

| Examples | Methyl formate % by weight (a) | Catalyst mol % (b) | $COCl_2$ mol % (b) | Time hours | Temperature °C. | % (c) by GC analysis (d) Unconverted formate | MDCME formed |
|---|---|---|---|---|---|---|---|
| 2 | 13 | TPPO 10 | 186 | 2 / 16 / 21 | 60 / 60–93 / 80 | 6 | 76 |
| 3 | 11.5 | TPPO 20 | 147 | 6.75 | 70–75 | 10 | 90 |
| 4 | 23.2 | TPPO 19.7 | 134 | 4 / 4 | 60 / 70–75 | 5 | 95 |
| 5 | 13 | DBF 10.5 | 153 | 7.50 / 20.50 | 50 / 50–70 | 46 | 31 |
| 6 | 13 | $TPPCl_2$ 25 | 150 | 7.5 | 70–75 | — | 98 |

DBF: N,N-dibutylformamide
$TPPCl_2$: triphenylphosphine dichloride

| Examples | Methyl formate % by weight (a) | Catalyst mol % (b) | COCl$_2$ mol % (b) | Time hours | Temperature °C. | % (c) by GC analysis (d) | |
|---|---|---|---|---|---|---|---|
| | | | | | | Unconverted formate | MDCME formed | a) in the mixture of methyl formate and o-dichlorobenzene
b) relative to methyl formate
c) relative to the initial quantity of formate
d) with a standard (C$_8$ alkane)

EXAMPLE 7

3.61 g of methyl formate and triphenylphosphine oxide bound on a resin, prepared by chlorination of 5.4 g of triphenylphosphine supported on polystyrene beads (3 mmol P/g) in 26.5 g of o-dichlorobenzene, are introduced into a reactor similar to that of Example 1 and the reaction mixture is then heated to 68° C.

7.5 g of phosgene are next introduced gradually over 2 hours while the temperature is maintained between 68° and 80° C. and heating is continued at this temperature for 9 hours. The degree of conversion of methyl formate to methyl 1,1-dichloromethyl ether, determined by GC, is 27%.

EXAMPLE 8

25.85 g (0.35 mol) of ethyl formate, 160 g of o-dichlorobenzene and 24.35 g (0.087 mol) of triphenylphosphine oxide are introduced into a reactor similar to that of Example 1 and the reaction mixture is then heated to about 71° C. 50 g (0.505 mol) of phosgene are next introduced over 7½ hours at a temperature of approximately 75° C. and heating is then continued at this temperature for approximately 3 hours.

The mixture is cooled to about 25° C., 30 g of chloroform are added, the temperature is lowered to −2° C. and the complex formed by the catalyst and the chloroform is removed by filtration.

GC analysis of the filtrate makes it possible to determine that the degree of conversion of ethyl formate to ethyl 1,1-dichloromethyl ether is 88% and the quantity of unconverted ethyl formate is 6%.

The filtrate is distilled at reduced pressure (boiling point: b.p.=35°–38° C./65–70 mm Hg and b.p.=56°–65° C./350 mm Hg). Ethyl 1,1-dichloromethyl ether is thus obtained in a 58% yield.

We claim:

1. Process for the preparation of methyl 1,1-dichloromethyl ether or of ethyl 1,1-dichloromethyl ether, characterized in that methyl formate or ethyl formate is reacted with phosgene, diphosgene, triphosgene or oxalyl chloride, or one of their mixtures, at a temperature of between 40° C. and 100° C., in the presence of a catalyst chosen from the group consisting of:

the trisubstituted phosphine oxides and sulphides of general formula (I)

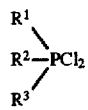

in which X denotes an oxygen or sulphur atom and R$^1$, R$^2$ and R$^3$, which are identical or different, denote a substituted or unsubstituted aromatic radical, the trisubstituted phosphine dichlorides of general formula (II)

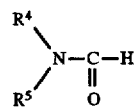

in which R$^1$, R$^2$ and R$^3$ have the abovementioned meaning, the formamides of general formula (III)

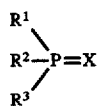

in which each of R$^4$ and R$^5$, which are identical or different, denotes a C$_4$–C$_{10}$ aliphatic radical or a cyclohexyl radical, the products of reaction of the formamides of formula (III) with chlorinating agents, and mixtures thereof.

2. Process according to claim 1, characterized in that phosgene is reacted with the formate.

3. Process according to claim 1, characterized in that the reaction mixture is liquid.

4. Process according to claim 3, characterized in that an organic solvent is employed which is inert towards the reactants, and chosen from chlorobenzene, dichlorobenzenes, trichlorobenzenes and xylenes.

5. Process according to claim 4, characterized in that the solvent is o-dichlorobenzene.

6. Process according to claim 1, characterized in that in the general formula (I) X denotes oxygen.

7. Process according to claim 1, characterized in that the substituents of the radicals R$^1$, R$^2$ and R$^3$ are chosen from the group consisting of: halogen atoms, C$_1$–C$_4$ alkyl and C$_1$–C$_4$ alkoxy radicals and the nitro group.

8. Process according to claim 1, characterized in that the catalysts of formula (I) or of formula (II) are bound to a polymer.

9. Process according to claim 1, characterized in that the catalyst is triphenylphosphine oxide.

10. Process according to claim 1, characterized in that R$^4$ and R$^5$, which are identical or different, denote the butyl or isobutyl radical.

11. Process according to claim 1, characterized in that the quantity of catalyst is between 5 and 50 mol % relative to the formate.

12. Process according to claim 1, characterized in that the compound which is reacted with the formate is added in stoichiometric quantity or in excess relative to the formate.

* * * * *